US007192604B2

(12) United States Patent
Brown et al.

(10) Patent No.: US 7,192,604 B2
(45) Date of Patent: Mar. 20, 2007

(54) IMPLANTABLE BIODEGRADABLE DEVICES FOR MUSCULOSKELETAL REPAIR OR REGENERATION

(75) Inventors: Kelly R. Brown, Hillsborough, NJ (US); Iksoo Chun, Flemington, NJ (US); Joseph J. Hammer, Bridgewater, NJ (US); Victor F. Janas, Monroe Township, NJ (US); Jennifer Mandanas, Painted Post, NY (US); Mora C Melican, Bridgewater, NJ (US); Alireza Rezania, Hillsborough, NJ (US); Mark C. Zimmerman, East Brunswick, NJ (US)

(73) Assignee: Ethicon, Inc., Somerville, NJ (US)

( * ) Notice: Subject to any disclaimer, the term of this patent is extended or adjusted under 35 U.S.C. 154(b) by 604 days.

(21) Appl. No.: 10/020,021

(22) Filed: Dec. 7, 2001

(65) Prior Publication Data

US 2002/0131989 A1 Sep. 19, 2002

Related U.S. Application Data

(63) Continuation-in-part of application No. 09/745,783, filed on Dec. 22, 2000.

(51) Int. Cl.
*A61K 9/70* (2006.01)
*A61L 15/64* (2006.01)

(52) U.S. Cl. ...................... 424/422; 424/423; 424/400; 424/443

(58) Field of Classification Search ................ 424/443, 424/444, 484–88, 402, 422, 423, 400
See application file for complete search history.

(56) References Cited

U.S. PATENT DOCUMENTS

| 4,655,777 | A | 4/1987 | Casper et al. |
| 5,512,600 | A | 4/1996 | Mikos et al. |
| 5,520,916 | A | 5/1996 | Dorigatti et al. |
| 5,522,895 | A | 6/1996 | Mikos |
| 5,674,286 | A | 10/1997 | Muth et al. |
| 5,759,830 | A | 6/1998 | Vacanti et al. |
| 5,769,899 | A | 6/1998 | Schwartz et al. |
| 5,770,193 | A | 6/1998 | Vacanti et al. |
| 5,770,417 | A | 6/1998 | Vacanti et al. |
| 5,842,477 | A | 12/1998 | Naughton et al. |
| 5,856,367 | A | 1/1999 | Barrows et al. |
| 6,350,284 | B1 * | 2/2002 | Tormala et al. .......... 623/17.19 |

FOREIGN PATENT DOCUMENTS

| EP | 1064958 A | 1/2001 |
| WO | WO84/04311 A1 | 11/1984 |
| WO | WO92/10218 A1 | 6/1992 |
| WO | WO95/33821 A1 | 12/1995 |
| WO | WO99/01538 A1 | 1/1999 |
| WO | WO99/09149 A1 | 2/1999 |
| WO | WO99/17817 A1 | 4/1999 |
| WO | WO99/48541 A1 | 9/1999 |
| WO | WO 0047245 A | 8/2000 |

OTHER PUBLICATIONS

PCT International Search Report, PCT/US01/49017, Aug. 23, 2002.

* cited by examiner

*Primary Examiner*—Edward J. Webman (57) ABSTRACT

An implantable biodegradable device is disclosed containing a fibrous matrix, the fibrous matrix being constructed from fibers A and fibers B, wherein fibers A biodegrade faster than fibers B, fibers A and fibers B are present in relative amounts and are organized such that the fibrous matrix is provided with properties useful in repair and/or regeneration of mammalian tissue.

28 Claims, 9 Drawing Sheets

IMPLANTABLE BIODEGRADABLE DEVICES FOR MUSCULOSKELETAL REPAIR OR REGENERATION

This application is a continuation-in-part of pending U.S. patent application Ser. No. 09/745,783, filed Dec. 22, 2000.

FIELD OF THE INVENTION

The present invention relates to biodegradable, implantable devices, e.g. tissue scaffolds which facilitate tissue infiltration there through, for the repair or regeneration of diseased or damaged musculoskeletal tissue.

BACKGROUND OF THE INVENTION

There is a clinical need for biocompatible and biodegradable structural matrices that facilitate tissue infiltration to repair/regenerate diseased or damaged tissue. In general, the clinical approaches to repair damaged or diseased musculoskeletal tissue, such as bone, cartilage, or muscle, do not substantially restore the original function of the tissue. Prosthetic joints/devices often have been used to treat such defects with mixed outcomes attributed to loosening, limited durability, and loss of functional tissue surrounding the defect. Thus, there remains a strong need for alternative approaches for tissue repair/regeneration that avoid the common problems associated with current clinical approaches.

The recent emergence of tissue engineering may offer alternative approaches to repair and regenerate damaged/diseased tissue. Tissue engineering strategies have explored the use of biomaterials in combination with cells and/or growth factors to develop biological substitutes that ultimately can restore or improve tissue function. The use of colonizable and remodelable scaffolding materials has been studied extensively as tissue templates, conduits, barriers, and reservoirs. In particular, synthetic and natural materials in the form of foams, sponges, gels, hydrogels, textiles, and nonwovens have been used in vitro and in vivo to reconstruct/regenerate biological tissue, as well as deliver chemotactic agents for inducing tissue growth.

Regardless of the composition of the scaffold and the targeted tissue, the template must possess some fundamental characteristics. The scaffold must be biocompatible, possess sufficient mechanical properties to resist crumbling at the time of surgery, highly porous to allow cell invasion, or growth, easily sterilized, able to be remodeled by invading tissue, and degradable as the new tissue is being formed. Furthermore, the scaffold may be fixed to the surrounding tissue via mechanical means, fixation devices, or adhesives. So far, conventional materials, alone or in combination, lack one or more of the above criteria.

Accordingly, there is a need for scaffolds that can resolve the potential pitfalls of conventional materials. These scaffolds combine different biocompatible materials to form a superior matrix for musculoskeletal tissue repair without resorting to undesirable and expensive ex vivo cell culturing and/or biological growth factor techniques.

SUMMARY OF THE INVENTION

Implantable, biodegradable devices of the present invention comprise a fibrous matrix comprising first fibers A and second fibers B, wherein fibers A biodegrade faster than fibers B and wherein fibers A and fibers B are present in relative amounts and are organized such that the fibrous matrix is provided with properties useful, desirable or required for use in the repair and/or regeneration of mammalian tissue.

DETAILED DESCRIPTION OF THE INVENTION

The present invention includes bioabsorbable, implantable medical devices containing a fibrous matrix that possesses certain properties that are highly desirable, or even necessary, for use in the repair and/or regeneration of diseased or damaged musculoskeletal tissue in mammals.

The matrix must be biodegradable and resorbable by the body. The matrix must facilitate tissue in-growth in order for tissue to replace the resorbing matrix. In addition, the matrix must be capable of providing and maintaining structural support required for a particular device in a particular procedure for so long as is required to effect the repair and/or regeneration of the tissue, including that time in which the matrix is being resorbed by the body. Accordingly, the rate of resorption of the fibrous matrix by the body preferably approximates the rate of replacement of the fibrous matrix by tissue. That is to say, the rate of resorption of the fibrous matrix relative to the rate of replacement of the fibrous matrix by tissue must be such that the structural integrity, e.g. strength, required of the scaffold is maintained for the required period of time. If the fibrous matrix degrades and is absorbed unacceptably faster than the matrix is replaced by tissue growing therein, the scaffold may exhibit a loss of strength and failure of the device may occur. Additional surgery then may be required to remove the failed scaffold and to repair damaged tissue. Thus, devices of the present invention advantageously balance the properties of biodegradability, resorption, structural integrity over time and the ability to facilitate tissue in-growth, each of which is desirable, useful or necessary in tissue regeneration or repair. Such devices provide synergistic improvements over devices of the prior art.

Examples of such devices include tissue scaffolds as exemplified herein. The scaffolds facilitate tissue infiltration therein and ultimately are biodegraded and resorbed by the body when placed in the body of a mammal. The scaffolds comprise a fibrous matrix constructed from at least two different fibrous materials, e.g. fibers, one of which biodegrades faster than the other. The fibers are of such composition and structure and are combined, or organized, in such a way, both with respect to relative fiber amounts and matrix structure, that the response of musculoskeletal tissue to the scaffold is enhanced and, in fact, infiltration and growth of musculoskeletal tissue therein is facilitated. In this way, the biodegrading scaffold fibrous matrix may be replaced by tissue at a rate that maintains the structural integrity of the scaffold throughout the treatment period.

Biodegradable polymers that may be used to prepare fibrous matrices and fibers used to prepare same are selected from the group consisting of aliphatic polyesters, poly(amino acids), copoly(ether-esters), polyalkylene oxalates, polyamides, poly(iminocarbonates), polyorthoesters, polyoxaesters, polyamidoesters, poly(anhydrides), polyphosphazenes and biopolymers. Certain of the polyoxaester copolymers further comprise amine groups.

Biodegradable and bioabsorbable glasses that may be used to prepare fibers and fibrous matrices may be selected from the group consisting of biologically active glasses comprising a silicate-containing calcium phosphate glass, e.g. BIOGLASS™ (University of Florida, Gainesville, Fla.), or calcium phosphate glasses wherein some of the calcium ions are replaced by varying amounts of iron, sodium, magnesium, potassium, aluminum, zirconium or other ions. This partial replacement of calcium ions is used to control the resorption time of the glass. For example, in a calcium phosphate glass, with a phosphate concentration between about 50 and about 70 weight percent, substituting iron for calcium, e.g. from about 0 weight percent to about 35 weight percent iron, while keeping the phosphate level constant, will increase the time for the glass to degrade and resorb in the body.

In addition, the present invention embodies a construct comprising porous biocompatible constructs having interconnecting pores or voids to facilitate the transport of nutrients and/or invasion of cells into the scaffold. The interconnected voids range in size from about 20 to 400 microns, preferably 50 to 250 microns, and constitute about 70 to 95 percent of the total volume of the construct. The range of the void size in the construct can be manipulated by changing process steps during construct fabrication.

In devices according to the present invention, the fibrous matrix comprises an organized network selected from the group consisting of threads, yarns, nets, laces, felts and nonwovens. A preferred method of combining the bioabsorbable fibrous materials, e.g. fibers, to make the fibrous matrix for use in devices of the present invention is known to one skilled in the art as the wet lay process of forming nonwovens. The wet lay method has been described in "Nonwoven Textiles," by Radko Krcma, Textile Trade Press, Manchester, England, 1967 pages 175–176, the contents of which are incorporated herein by reference.

In one embodiment of the invention, a continuous multifilament yarn (Yarn A) is formed from a copolymer comprising from about of 50 to about 95 weight percent PGA and from about 5 to about 50 weight percent PLA. Yarn A is cut into uniform lengths between ¼" and 2". Fiber in this form is known as "staple fiber". In a similar fashion, a continuous multifilament yarn (Yarn B) is formed from a copolymer comprising from about 2 to about 50 weight percent PGA and from about 50 to about 98 weight percent PLA. Yarn B is cut into uniform lengths of between ¼" and 2" staple fiber. Both Yarn A and Yarn B comprise filaments of from about 2 to about 200 microns in diameter, preferably from about 5 to about 100 microns.

In another embodiment of the invention, a continuous multifilament yarn (Yarn A) is formed from a biodegradable glass comprising about 65.9 weight percent $P_2O_5$, about 17.0 weight percent CaO and about 17.1 weight percent iron. The glass filament diameter was approximately 15 to 30 microns. In a similar fashion, a continuous multifilament yarn (Yarn B) is formed from biodegradable glass fibers comprising 25 about 60 weight percent $P_2O_5$, about 34 weight percent iron, about 5.7 weight percent CaO and about 0.3 percent impurities. All of these filaments were cut into uniform lengths of 0.5-inch staple fiber. Both Yarn A and Yarn B comprise filaments of from about 2 to about 200 microns in diameter, preferably from about 5 to about 100 microns.

It should also be understood that Yarn A could comprise a continuous multifilament yarn formed from a biodegradable polymer, while Yarn B could comprise a continuous multifilament yarn formed from a biodegradable glass.

Likewise, Yarn A could comprise a continuous multifilament yarn formed from a biodegradable glass, while Yarn B could comprise a continuous multifilament yarn formed from a biodegradable polymer. The key is that Yarn A biodegrades faster than Yarn B.

Predetermined amounts of staple fiber produced from Yarn A and Yarn B are dispersed into water. The predetermined relative amounts of Yarn A and B are selected in order to provide the fibrous matrix to be fabricated from the organized Yarn A and B with properties noted herein. Preferably, the weight ratio of fibers, e.g. Yarn A, to fibers, e.g. Yarn B, will range from about 19:1 to about 1:19, more preferably from about 9:1 to about 1:9.

The predetermined amounts of fibers from Yarn A and Yarn B, respectively, will vary depending upon, for example, the composition of the respective fibers, the construction of the respective fibers, and the particular organization of the respective fibers, which determines the structure of the fibrous matrix produced from the organized fibers. Considering such factors, the relative amounts of fibers are selected such that the matrix prepared therefrom not only possesses the structural integrity, i.e. strength, required for its intended purpose in tissue repair and/or regeneration, but also enhances tissue growth and infiltration into the matrix. In addition, the selection must be such that the rate of resorption of the biodegradable fibrous matrix approximates the rate of replacement of the fibrous matrix by tissue when placed in the body, thus preserving the structural integrity of the implant throughout the treatment period.

Additional processing aids, such as viscosity modifiers, surfactants and defoaming agents, may be added to the water. The purpose of such processing aids is to allow a uniform dispersion of the filaments within the water without causing foaming, which in turn may cause defects in the final product.

A bioabsorbable thermoplastic polymer or copolymer, such as Polycaprolactone (PCL) in powder form, also may be added to the water. This powder possesses a low melting temperature and acts as a binding agent later in the process to increase the tensile strength and shear strength of the nonwoven structure, or fibrous matrix. The preferred particulate powder size of PCL is in the range of 10–500 microns in diameter, and more preferably 10–150 microns in diameter. Additional binding agents include biodegradable polymeric binders selected from the group consisting of polylactic acid, polydioxanone and polyglycolic acid.

Figure 1A:
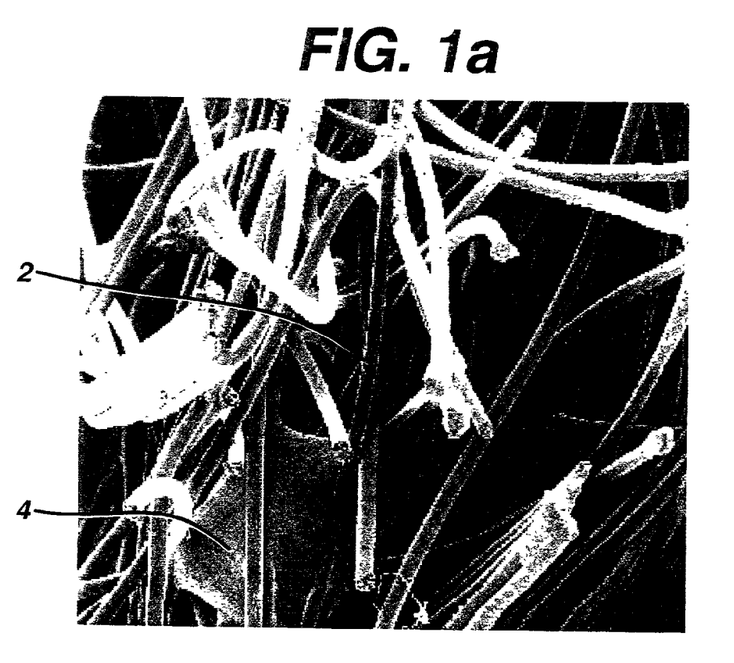
FIGS. 1a and 1b are photographs of a nonwoven fibrous matrix utilizing polycaprolactone (PCL) as a binding agent.
Figure 1B:
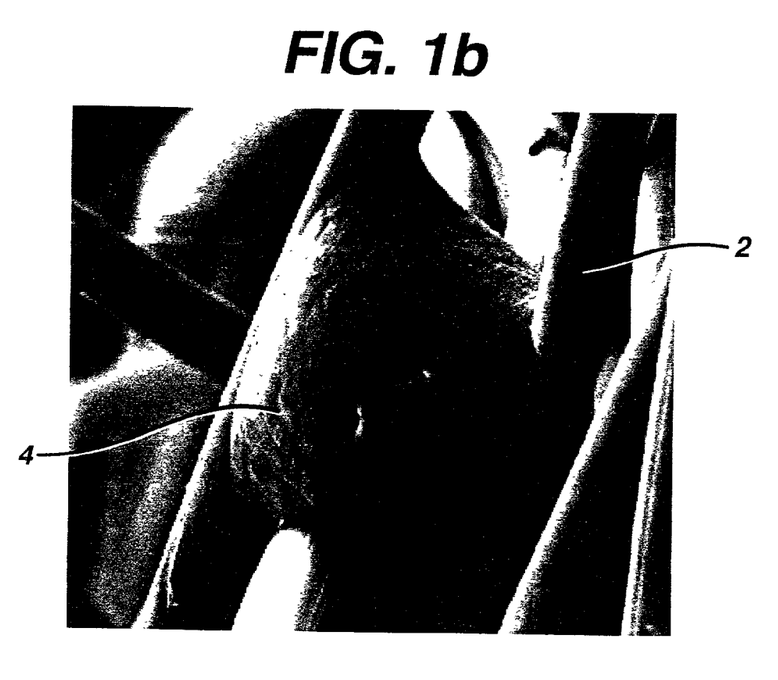

Once the fibers are uniformly dispersed within the water, the mixture is drained through a screen. The screen allows water to pass through, but traps the fiber. If PCL powder is included in the mixture, some of the powder is trapped as well within the organized mat of fibers. After the water has drained through the screen, the mat of fibers is removed. The mat containing PCL powder fibers is then subjected to heat in order to melt the PCL. The melt temperature range is between about 60° C. and about 100° C., preferably between 60–80° C. It is crucial to perform this step at a temperature that is above the melting point of PCL powder or similar binding agent, and below the softening point of the fibers. This is necessary to avoid damaging the staple fibers. The powder is melted, flows around the filaments and subsequently cools to a solid state. As seen in FIG. 1, fibers 2 are bonded together at intersecting points via particles 4 of binding agent when the molten powder returns to a solid state. Thus the intersecting fibers are encapsulated at that point in solid polymer and locked in place. The powder thus acts as a binding agent, increasing the strength of the matrix.

The matrix is rinsed overnight in water, followed by another overnight incubation in ethanol to remove any residual chemicals or processing aids used during the manufacturing process. The matrix may then be sterilized by a number of standard techniques, such as exposure to ethylene oxide or gamma radiation.

The nonwoven fibrous matrices of the present invention may be formed into different shapes, or configurations, such as disks, rectangles, squares, stars and tubes, by thermal or non-thermal punching of the nonwoven sheets with dies of appropriate shape and dimension.

Tubular structures having gradient degradation profiles also are included among devices of the present invention. In vascular grafts, having a tube with pores in the outer diameter which transitions to smaller pores on the inner surface, or visa versa, may be useful in the culturing of endothelial cells and smooth muscle cells for the tissue culturing of vessels.

Multilayered tubular structures that allow the regeneration of tissue that mimics the mechanical and/or biological characteristics of blood vessels will have utility as vascular grafts. Concentric layers, made from different fiber compositions under different processing conditions, could have tailored mechanical properties, bioabsorption properties and tissue in-growth rates. The inner, or luminal, layer would be optimized for endothelialization through control of the porosity of the surface and the possible addition of a surface treatment. The outermost, or adventitial, layer of the vascular graft would be tailored to induce tissue in-growth, again by optimizing the porosity (percent porosity, pore size, pore shape and pore size distribution) and by incorporating bioactive factors, pharmaceutical agents, or cells. There may or may not be a barrier layer with low porosity disposed between these two porous layers to increase strength and decrease leakage.

The biodegradable fibers used to prepare fibrous matrices and devices according to the present invention may be solid, or hollow, or may be of a sheath/core construction. Filaments may be co-extruded to produce a sheath/core construction. Additionally, such constructs may be formed by coating a biodegradable fiber, e.g. a biodegradable glass fiber, with a biodegradable polymer. Methods for making each construct of filament are well known to those skilled in the art. In a co-extruded construction, each filament comprises a sheath of biodegradable polymer that surrounds one or more cores comprising another biodegradable polymer. Filaments with a fast-absorbing sheath surrounding a slow-absorbing core may be desirable in instances where extended support is necessary for tissue in-growth.

A further embodiment may include fibers with circular cross-section comprising a combination of fibers ranging from rapidly to slowly resorbing fibers. It has been observed that, in a large articular cartilage defect (7 mm) in a goat model, cartilage formation occurs at the periphery of the rapidly degrading implant. However, the center of the implant was devoid of tissue because the scaffold resorbed too quickly to allow cell migration from the periphery of the implant to the center. Having slower degrading fibers at the center of the defect would allow for complete filling of the defect by tissue in-growth, including the central portion. An example of such a system would be a nonwoven structure comprising a majority of fibers in the center that are prepared from a PLA-based polymer rich in PLA. The periphery would contain a majority of filaments prepared from a PGA-based polymer rich in PGA. Because the PLA-based polymer absorbs more slowly than the PGA-based polymer, the center of the structure will absorb at a slower rate than the periphery of the structure.

In yet another embodiment, the fibrous matrix may comprise a gradient structure. For example, a fibrous implant may have a gradual or rapid, but continues, transition from rapidly degrading fibers at the periphery of the implant, to slowly degrading fibers at the center, relatively speaking. In another embodiment, the transition may occur between the top of the matrix to the bottom of the matrix. One profile for transition from rapidly degrading fibers to slowly degrading fibers may be, for instance, from about 100% rapidly degrading fibers, to about 75% rapidly degrading fibers/25% slowly degrading fibers, to about 50% rapidly degrading fibers/50% slowly degrading fibers, to about 25% rapidly degrading fibers/75% slowly degrading fibers, to about 100% slowly degrading fibers, proceeding from the periphery of the implant to the center.

Figure 3:
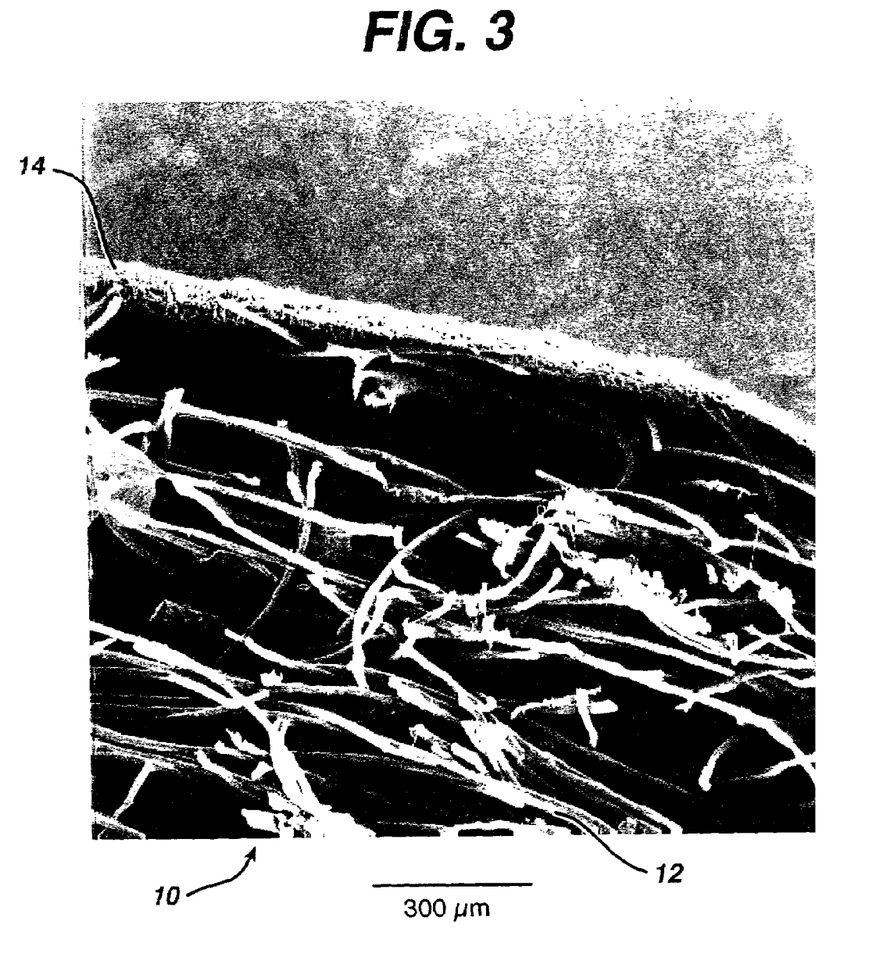
FIG. 3 is a micrograph of a biodegradable, nonwoven fibrous matrix having electrostatically deposited thereon a biodegradable, porous, fibrous and continuous layer.

In yet another embodiment, the three-dimensional structures of the present invention may be coated with a biodegradable, fibrous and porous polymer coating, e.g. a sheet, preferably produced by an electrostatic spinning process. As seen in FIG. 3, the fibrous matrix 10 comprising organized fibers 12 has applied to a surface thereof polymeric coating 14. The electrostatically spun polymer coating can provide the nonwoven matrices with enhanced mechanical properties and the ability to hold sutures. Exemplary biodegradable polymeric coats may be prepared from polymers selected from the group consisting of polylactic acid, polyglycolic acid, polycaprolactone and copolymers thereof.

Embodiments of the invention thus far describe a homogenous mixture of filaments in the form of a sheet, or nonwoven matrix. However, the mixture need not be homogenous and the final form need not be a sheet.

A non-homogenous mixture of filaments may be desirable in applications where total absorption time and/or loss of strength over time varies throughout the material.

Therefore, in yet another embodiment, a multi-layered device comprising a first layer that comprises a majority of filaments prepared from a (90/10) PGA/PLA copolymer and second layer that comprises a majority of filaments prepared from a (95/5: wt/wt) PLA/PGA copolymer, will provide a structure that, when implanted, will have a first, e.g. top, layer that is absorbed more quickly than the second, e.g. bottom, layer.

Similar structures may be produced in any shape. In other embodiments, cylinders or prisms with fast (or slow) absorbing cores may be produced during a nonwoven process by segregating the different filaments during the forming process.

In yet another embodiment of the invention, the porous nonwoven matrix can be chemically crosslinked or combined with hydrogels, such as alginates, hyaluronic acid, collagen gels, and poly(N-isopropylacrylamide).

In still another embodiment of the invention, the porous nonwoven matrix can be penetrated with a polymer melt or a polymer solvent solution. Such penetration provides the construct with the ability to maintain bundle coherence and retain potentially loose fibers. Biodegradable polymers that may be used to penetrate the porous nonwoven matrix are selected from the group consisting of aliphatic polyesters, poly(amino acids), copoly(ether-esters), polyalkylene oxalates, polyamides, poly(iminocarbonates), polyorthoesters, polyoxaesters, polyamidoesters, poly(anhydrides), polyphosphazenes and biopolymers.

In another embodiment of the invention, the matrix may be modified, either through physical or chemical means, to contain biological or synthetic factors that promote attachment, proliferation, differentiation, and/or matrix synthesis of targeted cell types. Furthermore, the bioactive factors may also comprise part of the matrix for controlled release of the factor to elicit a desired biological function. Growth factors, extracellular matrix proteins, and biologically relevant peptide fragments that can be used with the matrices of the current invention include, but are not limited to, members of TGF-β family, including TGF-β1, 2, and 3, bone morphogenic proteins (BMF-2, -12, and -13), fibroblast growth factors-1 and -2, platelet-derived growth factor-AA, and -BB, platelet rich plasma, vascular endothelial cell-derived growth factor (VEGF), plelotrophin, endothelin, tenascin-C, fibronectin, vitronectin, V-CAM, I-CAM, N-CAM, selectin, cadherin, integrin, laminin, actin, myosin, collagen, microfilament, intermediate filament, antibody, elastin, fibrillin, and fragments thereof, and biological peptides containing cell- and heparin-binding domains of adhesive extracellular matrix proteins such as fibronectin and vitronectin. The biological factors may be obtained either through a commercial source or isolated and purified from a tissue.

In yet another embodiment, the three-dimensional structures of the present invention can be seeded or cultured with appropriate cell types prior to implantation for the targeted tissue. Cells which can be seeded or cultured on the matrices of the current invention include, but are not limited to, bone marrow cells, stromal cells, stem cells, embryonic stem cells, chondrocytes, osteoblasts, osteocytes, osteoclasts, fibroblasts, pluripotent cells, chondrocyte progenitors, endothelial cells, macrophages, leukocytes, adipocytes, monocytes, plasma cells, mast cells, umbilical cord cells, mesenchymal stem cells, epithelial cells, myoblasts, and precursor cells derived from adipose tissue. The cells can be seeded on the scaffolds of the present invention for a short period of time, e.g. less than one day, just prior to implantation, or cultured for longer a period, e.g. greater than one day, to allow for cell proliferation and matrix synthesis within the seeded scaffold prior to implantation.

Cells typically have at their surface, receptor molecules which are responsive to a cognate ligand (e.g., a stimulator). A stimulator is a ligand which when in contact with its cognate receptor induce the cell possessing the receptor to produce a specific biological action. For example, in response to a stimulator (or ligand) a cell may produce significant levels of secondary messengers, like $Ca^{+2}$, which then will have subsequent effects upon cellular processes such as the phosphorylation of proteins, such as (keeping with our example) protein kinase C. In some instances, once a cell is stimulated with the proper stimulator, the cell secretes a cellular messenger usually in the form of a protein (including glycoproteins, proteoglycans, and lipoproteins). This cellular messenger can be an antibody (e.g., secreted from plasma cells), a hormone, (e.g., a paracrine, autocrine, or exocrine hormone), or a cytokine.

The unique properties of the matrices of the present invention can be shown by in vitro experiments that test for adhesion, migration, proliferation, and matrix synthesis of primary bovine chondrocytes by conventional culturing for 4 weeks followed by histological evaluation. The following examples are merely illustrative of the principles and practices of the present invention and are not intended to limit the scope of the invention.

EXAMPLE 1

This example describes the preparation of three-dimensional nonwoven fibrous matrices, or mats, according to the present invention.

A copolymer of PGA/PLA (90/10) was melt extruded into continuous multifilament yarn by conventional methods of making yarn and subsequently oriented in order to increase strength, elongation, and energy required to rupture. A copolymer of PLA/PGA (95/5) was also extruded into continuous multifilament yarn via conventional means and oriented using a different set of conditions to increase its physical properties. The yarns from both of these copolymer systems comprised filaments of approximately 20 microns in diameter. These yarns were then cut into uniform 0.5 inch lengths to form 0.5 inch staple fiber.

A number of wet lay nonwoven matrices were then prepared utilizing predetermined fiber selection as follows: (a) 100% of fiber prepared from the (90/10) PGA/PLA copolymer; (b) 100% of fiber prepared from the (95/5) PLA/PGA copolymer; (c) a fiber mixture of 50% by weight of fibers prepared from the (95/5) PLA/PGA copolymer and 50% by weight of fibers prepared from the (90/10) PGA/PLA copolymer.

During production of the nonwoven matrices, a total of twelve grams of staple fiber was dispersed into 1,926 cubic inches of water. The water was agitated to promote a uniform mixture. Processing aids were added to the water to allow a uniform dispersion of the filaments within the water without causing foaming. Processing aids used included 117 grams Nalco 625 liquid polymer (Nalco Chemical Company, Naperville, Ill.), 20 drops Value M-20 (Marubishi Oil Company, Limited, Osaka, Japan), and 5 drops Berchem 4283 (Bercen, Incorporated, a division of Cranston Print Works Company, Cranston, R.I.).

Once the fibers were uniformly dispersed within the water the mixture was drained through a screen to allow water to pass there through and to trap the fibers on the screen. After the water drained through the screen, the mat of fibers was removed. The mat was then dried on both sides. The mat was rinsed overnight in water followed by another overnight incubation in ethanol to remove any residual chemicals or processing aids used during the manufacturing process.

EXAMPLE 2

This example describes the preparation of three-dimensional nonwoven matrices, or mats, containing a binding agent. Staple fibers were prepared as described in Example 1. A number of nonwoven mats were then prepared utilizing fiber selection as follows: (a) 100 percent by weight (90/10) PGA/PLA; (b) 100 percent by weight (95/5) PLA/PGA; (c) 50/50 percent mix by weight of (90/10) PGA/PLA and (95/5) PLA/PGA; (d) 95/5 percent mix by weight of (90/10) PGA/PLA and (95/5) PLA/PGA; (e) 5/95 percent mix by weight of (90/10) PGA/PLA and (95/5) PLA/PGA; (f) 75/25 percent mix by weight of (90/10) PGA/PLA and (95/5) PLA/PGA; and (g) 25/75 percent mix by weight of (90/10) PGA/PLA and (95/5) PLA/PGA.

Medical grade Polycaprolactone (PCL) (Birmingham Polymers, Incorporated, Birmingham, Ala.) was sieved through a screen in order to filter out particles greater than 150 m in size. Twelve grams of staple fiber and 2.4–6.0 grams of PCL powder were dispersed into 1,926 cubic inches of water. Processing aids listed in Example 1 also were added.

Once the fibers were uniformly dispersed within the water, the mixture was drained through a screen. This screen allows water to pass through, but traps the fibers and PCL powder. After the water drained through the screen, the mat of fibers and PCL powder was removed. The mat was then placed in a container of water heated to approximately 80° C. in order to melt the PCL. The melt temperature of the particular PCL used ranges between about 60° C. and about 80° C. It is crucial to perform this step at a temperature that is above the melting point of PCL powder and below the softening point of the fibers in order to avoid damaging the staple fibers. The powder melts, flows around the filaments and cools to a solid state. When the molten powder returns to a solid state, some of the points where filaments intersect are encapsulated in solid polymer and locked in place (FIG. 1).

The mat was rinsed overnight in water followed by another overnight incubation in ethanol to remove any residual chemicals or processing aids used during the manufacturing process.

Nonwoven fibrous mats with and without PCL powder were tested for strength.

Testing was performed as follows: 8×50 mm specimens of the 50/50 mix nonwoven mats as noted herein above, containing different amounts of PCL binder (0 to 6 grams), were mechanically tested on an Instron 4201 (Canton, Mass.) using a 10 mm gauge length, a cross head speed of 25.4 mm/min, and a 20 lb. load cell. The mean peak loads for specimen with and without PCL binder is listed in the table below. In all cases, physical properties increased with the addition of PCL binder. In particular, a 20-fold increase in strength of the matrices according to the present invention was observed with addition of 6 grams of PCL binder particles. This enhancement was statistically significant at $p<0.05$ (Analysis of variance with Neuman-Keuls post-hoc).

| Polymer | Mean peak load (lb) | STDV | N |
|---|---|---|---|
| 50/50 mix (90/10) PGA/PLA and 95/5 PLA/PGA) with no binder | 0.095 | 0.035 | 9 |
| 50/50 mix (90/10) PGA/PLA and (95/5) PLA/PGA) with 2.4 g binder | 0.623 | 0.136 | 9 |
| 50/50 mix (90/10) PGA/PLA and (95/5) PLA/PGA) with 6.0 g binder | 2.186 | 0.558 | 9 |

EXAMPLE 3

This example describes the preparation of three-dimensional nonwoven matrices, or mats, containing absorbable glass fibers.

Staple fibers of (90/10) PGA/PLA and (95/5) PLA/PGA were produced as described in example 1. In addition, absorbable glass fibers were used to form nonwoven mats. The absorbable glass fibers were composed of 50% phosphorous, 17% calcium, and 33% iron. The glass filament diameter was approximately 10–20 microns. All of these filament yarns were cut into uniform lengths of 0.5".

A number of wet lay nonwoven cylinders were prepared utilizing fiber selection as follows: (a) 100 percent of the fiber from the absorbable glass fiber; (b) a mixture of 50 percent by weight of the fiber from the absorbable glass fiber and 50 percent by weight of the fiber from the (90/10) PGA/PLA copolymer; (c) a mixture of 50 percent by weight of the fiber from the absorbable glass fiber and 50 percent by weight of the fiber from the (95/5) PLA/PGA copolymer filaments; and (d) a mixture of 50 percent of the fiber by weight from the absorbable glass fiber, 25 percent by weight of the (95/5) PLA/PGA copolymer and 25 percent by weight of the (90/10) PGA/PLA copolymer.

The nonwoven structures in cylinder form were prepared in accordance with example 1, except that absorbable glass filaments were incorporated into the structure, and a rigid plastic tube was used to contain the water/fiber slurry while it drained onto the forming screen. As the water drained through the forming screen, a circular sheet was formed which thickened until a cylinder was formed.

Each of the above was produced utilizing the PCL binder. The 100% glass material was also produced without PCL binder. As noted in example 2, the structural integrity of the cylinder increased with the addition of PCL binder.

Figure 6:
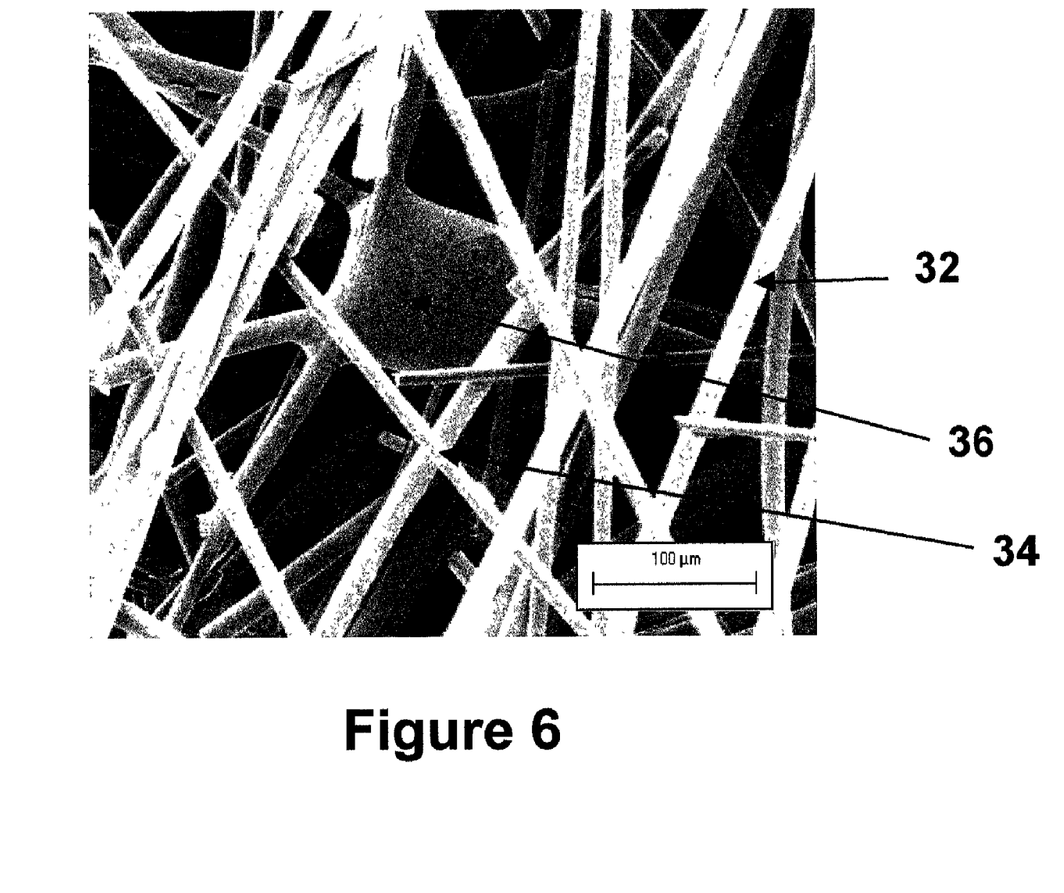
FIG. 6 is a micrograph of a nonwoven fiberous matrix comprising glass and polymer, and utilizing polycaprolactone (PCL) as a binding agent.

FIG. 6 is a micrograph of a nonwoven structure wherein about 50 percent of the fiber by weight is the absorbable glass fiber, about 25 percent by weight of the fiber is the (95/5) PLA/PGA copolymer and about 25 percent by weight of the fiber is the (90/10) PGA/PLA copolymer. The figure shows both polymer fibers 32 and glass fibers 34, as well as binder 36 holding fibers together.

EXAMPLE 4

This example illustrates that the ratio of different biodegradable fibers fabricated by the process described in Example 1 and 2 affects the invasion and maintenance of chondrocyte phenotype.

Materials and Methods

Cells:

Primary chondrocytes were isolated from bovine shoulders as described by Buschmann, M. D. et al. (J. Orthop. Res. 10, 745–752, 1992). Bovine chondrocytes were cultured in Dulbecco's modified eagles medium (DMEM-high glucose) supplemented with 10% fetal calf serum (FCS), 10 mM HEPES, 0.1 mM nonessential amino acids, 20 g/ml L-proline, 50 g/ml ascorbic acid, 100 U/ml penicillin, 100 g/ml streptomycin and 0.25 g/ml amphotericin B (growth media). Half of the medium was replenished every other day.

Scaffolds:

1 cm×1 cm squares were cut from nonwoven polymer sheets prepared from 100 weight percent (90/10) PGA/PLA, 100 weight percent (95/5) PLA/PGA, and 50/50 percent mix by weight of (90/10) PGA/PLA and (95/5) PLA/PGA) prepared as described in example 1. Scaffolds were sterilized for 20 minutes in 70% ethanol followed by five rinses of phosphate-buffered saline (PBS).

Seeding Method:

Freshly isolated bovine chondrocytes were seeded at $5 \times 10^6$ cells (in 50 µl medium) by a static seeding method in hydrogel-coated plates (ultra low cluster dishes, Costar). Following 6 hours of incubation in a humidified incubator, the scaffolds were replenished with 2 ml of growth media. The scaffolds were cultured statically for additional 4 days, followed by culturing in a rotating bioreactor (Syntecon, model: STLV, Houston, Tex.) for additional 24 days (4 weeks total culture time).

Histology:

Constructs harvested at various time points (4, 14, 21, and 28 days) were fixed in 10% buffered formalin, embedded in paraffin and sectioned. Sections were stained with Hematoxylin eosin (H/E; cell number and morphology) or Safranin-O (SO; sulfated glycosaminoglycans-GAG's). Two samples per time point were sectioned and stained.

Figure 2A:
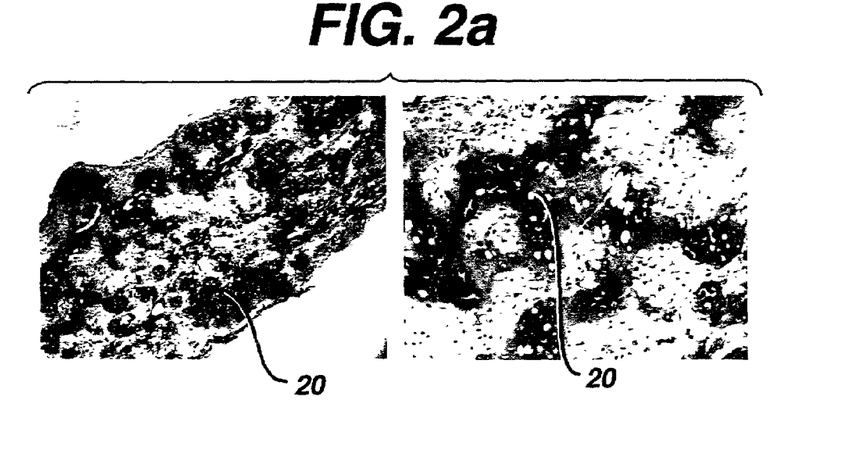
FIGS. 2a–2c are photographs of Safranin-O sections of tissue scaffolds prepared from (90/10) Polyglycolic Acid (PGA)/Polylactic Acid (PLA) filaments (2c); (95/5) PLA/PGA filaments (2b); and a 50/50 weight ratio blend of (90/10) PGA/PLA and (95/5) PLA/PGA filaments (2a), respectively, each scaffold invaded with chondrocytes following 4 weeks of culturing.
Figure 2B:
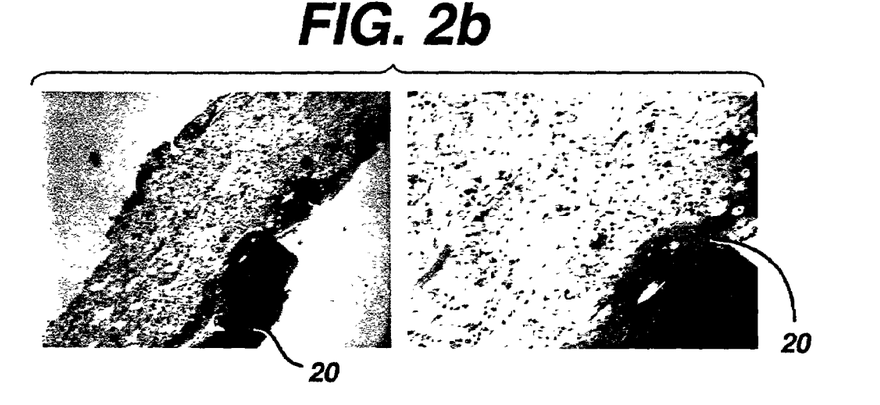
Figure 2C:
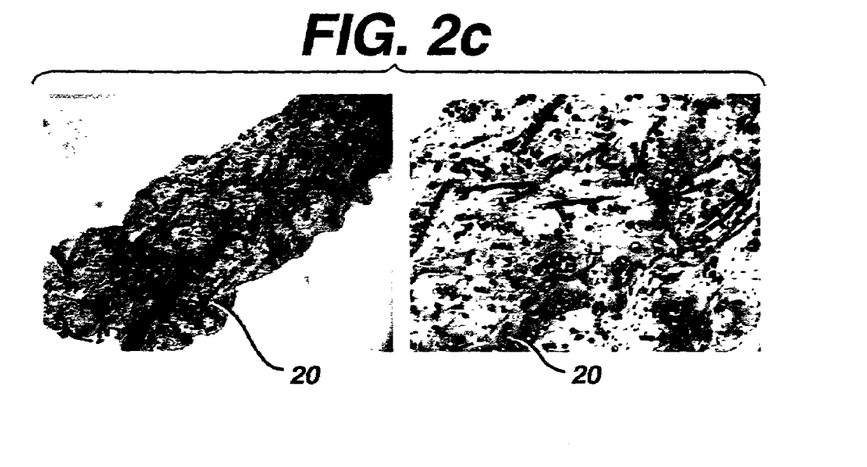

Results:

As shown in FIGS. 2a–2c, following 28 days of culture under bioreactor conditions, the architecture of the scaffolds allowed cell migration and cell matrix synthesis throughout the cross section of the nonwoven matrices. However, distinct differences in sulfated GAG synthesis were evident among the scaffolds, as indicated by the staining patterns produced in the respective scaffolds shown in FIGS. 2a–2c. Staining for synthesized GAG 20 was present throughout the 50/50 mix scaffolds (FIG. 2a) in contrast to (90/10) PGA/PLA (FIG. 2c) and (95/5) PLA/PGA scaffolds FIG. (2b). Evaluation of the histology sections by image analysis indicated enhanced sulfated GAG production in 50/50 mix (about 50% surface covered by GAG) as compared to (95/5) PLA/PGA (about 10% surface covered by GAG) and (90/10) PGA/PLA (about 32% surface covered by GAG). Note, although it appears that the intensity of SO staining for the (90/10) PGA/PLA and 50/50 mix were similar, approximately 26% of the stained area for the (90/10) PGA/PLA scaffolds was due to nonspecific staining originating from degrading PGA fibers.

EXAMPLE 5

This example describes another embodiment of the present invention in which the preparation of a hybrid structure of a nonwoven mesh and microfibrous fabric is described.

A nonwoven sheet comprising a 50/50 mix of (90/10) PGA/PLA and (95/5) PLA/PGA was prepared as described in Example 2. The sheet, 1 inch by 3 inches in size, was rolled around a metal tube with a diameter of about one inch to form a nonwoven cylinder. The ends of the cylinder were secured using an electrical insulating tape.

A custom-made electrostatic spinning machine located at Ethicon Incorporated (Somerville, N.J.) was then used to cover the nonwoven cylinder with microfibrous biodegradable fabric. Spellman high voltage DC supply (Model No.: RHR30PN30, Spellman High Voltage Electronics Corporation, Hauppauge, N.Y.) was used as high voltage source for the spinning machine. Applied voltage as driving force and the speed of mandrel were controlled by the Labview™ computer software. Distance between the spinneret and the mandrel was mechanically controlled.

The nonwoven cylinder was mounted onto a rotating conductive mandrel that acted as a ground. The ends of the mandrel not covered by the nonwoven substrate were masked with an insulating tape to prevent the attraction of the microfibers to the ends. A 15% solution of a (60/40) PLA/PCL copolymer was prepared in Trichloroethane (TCE). The polymer solution was placed into a spinneret and high voltage was applied to the polymer solution. This experiment was performed at ambient temperature and humidity.

The operating conditions during spinning were as follows:

| | |
|---|---|
| Spinneret voltage | 16,000 V |
| Mandrel voltage | Grounded |
| Mandrel speed | 100 rpm |
| Spinneret to mandrel distance | 10 cm |

This process resulted in a deposited porous elastomeric polymer of approximately 10–500 microns in thickness on the surface of the nonwoven cylinder. FIG. 3 shows a micrograph of a biodegradable nonwoven matrix 10 with an electrostatically deposited biodegradable, porous, and continuous layer 14, or sheet. The electrostatically spun fabric provides the nonwoven matrices with enhanced mechanical properties and the ability to hold sutures.

EXAMPLE 6

This example describes the in vitro degradation of the nonwoven meshes.

Nonwoven sheets of 90/10 PGA/PLA, 95/5 PLA/PGA, and 50/50 mix of 90/10 PGA/PLA and 95/5 PLA/PGA were prepared as described in Example 2. A die cutter was used to prepare 0.5 cm×1.5 cm pieces of the nonwovens, which were placed in individual tubes filled with 50 ml of PBS. The tubes were placed in a 37° C. water bath for 1, 2, 3, 4, 8, 12, and 24 weeks, respectively. At the end of the designated time periods the test articles were removed from the tubes containing buffer, rinsed with 500 ml of DI water, and partially dried. This was repeated one more time. The samples were placed in plastic bags and dried in a vacuum oven for 2 days, and weighed to the nearest 0.1 mg.

Figure 4:
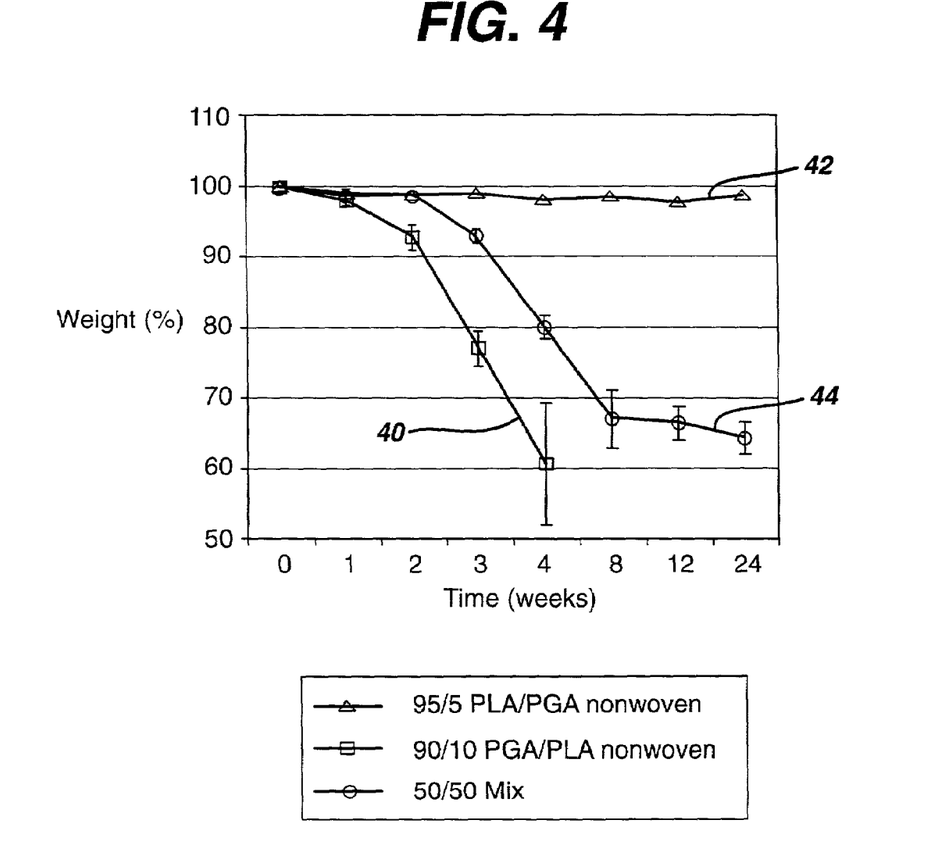
FIG. 4 is a plot of the mass loss for scaffolds prepared from (95/5) PLA/PGA, (90/10) PGA/PLA, 50/50 blend of (95/5) PLA/PGA and (90/10) PGA/PLA nonwovens.

Results:

The degradation profile of the three nonwoven compositions is depicted in FIG. 4. For the 90/10 PGA/PLA samples 40 the data collection was stopped following 4 weeks because the samples had lost their structural integrity, which contributed to the large deviation in the sample weights. The mass loss of the 95/5 PLA/PGA samples 42 was nearly constant during the 24 week study. The 50/50 mix samples 44 showed a similar mass loss profile as the 90/10 PGA/PLA samples, however following 8 weeks the mass loss had plateaued, indicating that the majority of the 90/10 PGA/PLA fibers had resorbed, thus leaving the 95/5 PLA/PGA fibers and the PCL binder.

EXAMPLE 7

This example describes the in vivo evaluation of three-dimensional nonwoven mats containing absorbable glass fibers as bone replacement materials.

Fibrous glass scaffolds comprised of 50 percent glass, 25 percent (90/10) PGA/PLA, and 25 percent wt/wt (95/5) PLA/PGA fibers were prepared as described in Example 3. The fibrous matrix was tested for bone growth potential using a well-document rabbit radial defect model. This model is widely used in orthopedic research for the screening of bone graft materials and substitutes. Radiographic analysis was used six weeks after surgery to assess bone healing.

Experimental Design

Sixteen skeletally mature New Zealand White rabbits were used to assess differences in bone in-growth into three different groups of material. Each group was taken out to eight weeks. The groups are outlined below:
1. Positive control—autograft bone
2. Negative control—empty defect
3. Glass/polymer nonwoven scaffold The positive control was autograph bone that was been homogenized to produce a paste-like substance. The negative control was an empty defect. Each animal received either an implant placed in a critical sized, i.e. unable to spontaneously heal, defect in the right radius of the forelimb or the defect was left unfilled. A radial defect was created by removing a 1.5-cm length of the midshaft radius. This was replaced with the test article, or left unfilled, and sutured closed. Post-operatively, radiographs were taken to evaluate the radiectomy and the position of the materials implanted at the site. At 6 weeks post-surgery, radiographs were again taken.

Method

The animals, e.g. rabbits, used in this example were handled and maintained in accordance with current requirements of the Animal Welfare Act. Animals were weighed in kilograms prior to any procedures and this weight used to calculate all drug doses. An analgesic, buprenorphine hydrochloride, was administered subcutaneously at a dose 0.02 mg/kg about 2–3 hours before the start of the surgery. Each rabbit was anesthetized with an intramuscular (IM) injection of intramuscular injections of ketamine hydrochloride (35 mg/kg) acepromazine maleate (0.75 mg/kg), and xylazine (5 mg/kg). Preoperative radiographs of the bilateral forearms were taken.

Depilation of the surgical site was accomplished with an electric clipper equipped with a surgical shaving blade. Following rinsing with alcohol and drying, the entire area was painted with an aqueous iodophore solution of 1 percent available iodine. The anesthetized and surgically prepared animal was placed on a surgical table in the supine position. Sterile drapes were applied to the prepared area using aseptic technique.

A longitudinal incision was made over the radial bone at the middle one third of the right front leg. The periosteum was separated from the muscle and a 15 mm defect, located approximately 2.0 to 2.5 cm proximal to the radiocarpal joint, was produced using a powered oscillating saw. The periosteum was removed and thoroughly washed with saline prior to placement of the test articles. The defect was then either filled with a device according to the present invention, or with autograph bone, or left unfilled. Due to the strutting of the forelimb by the ulna, no additional fixation or hardware was necessary to stabilize the limb. All the incisions were closed with multiple layers of resorbable suture upon completion of the operation. Post-operatively, radiographs were taken to evaluate the radiectomy and the position of the materials implanted at the site.

The rabbits were allowed to ambulate freely following recovery from anesthesia. At six weeks, the animals were weighted just prior to sacrifice. The animals were euthanized with an intravenous injection of EUTHASOLR (Delmarva Laboratories, Inc., Midlothian, Va. 23113) at a dosage of 0.3 ml/kg of body weight. A radiograph of the bilateral forearms was taken.

Results

Figure 5A:
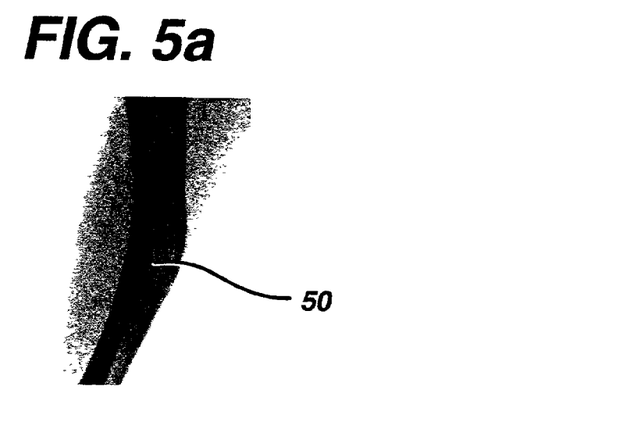
FIGS. 5a–5c are radiographic images of a rabbit radial defect six weeks after implantation of autograft bone (5a), or a nonwoven fibrous matrix construct according to the present invention (5b), or with no implant (5c).
Figure 5B:
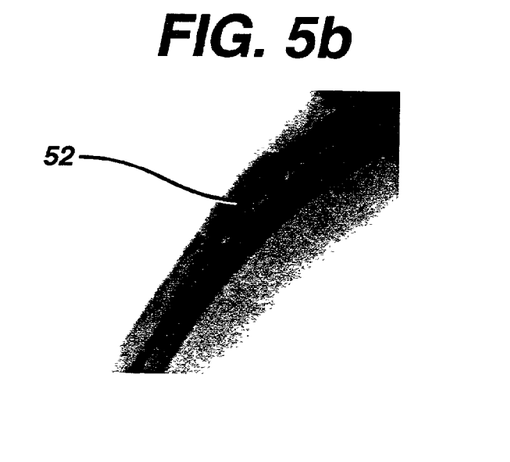
Figure 5C:
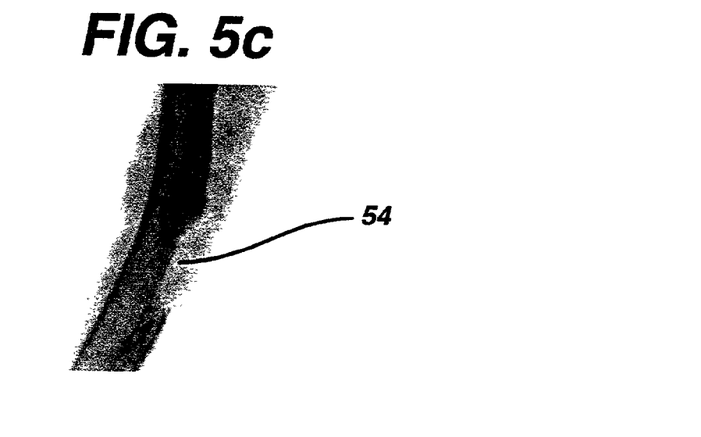

As shown in FIGS. 5a–5c, radiographs taken six weeks after implantation showed differences in the bony in-growth into the defects in the radius. The healing positive control is pictured in FIG. 5a, where it can be seen that autograph bone 50 has effectively filled the defect. As seen in the non-filled negative control depicted in FIG. 5c, There was no bony in-growth evident in the empty defect 54. In contrast, the fibrous glass matrix promoted bone healing, as evidenced by the radioopaque callus 52 apparent in FIG. 5b.

EXAMPLE 8

This example describes the preparation of three-dimensional nonwoven matrices, or mats, containing absorbable glass fibers of two different compositions. The glass compositions differ in resorption rate in vivo.

The first absorbable glass fibers comprise 65.9 weight percent $P_2O_5$, 17.0 weight percent CaO and 17.1 weight percent iron. The glass filament diameter was approximately 15 to 30 microns. The second absorbable glass fibers comprise 60 weight percent $P_2O_5$, 34 weight percent iron, 5.7 weight percent CaO and 0.3 percent impurities. The glass filament diameter was approximately 10 to 20 microns. All of these filaments were cut into uniform lengths of 0.5 inch. The second absorbable glass fiber, by virtue of the higher iron content absorbs slower in vivo than the first absorbable glass fiber.

A wet-lay nonwoven mat was prepared utilizing a fiber selection as follows: (a) 50 weight percent of the fiber from the first absorbable glass fiber, and (b) 50 weight percent of the fiber from the second absorbable glass fiber.

The nonwoven structures in mat form were prepared in accordance with the procedure described in Example 2, utilizing PCL binder. As the water drained through the forming screen, a nonwoven felt mat was formed.

Figure 7:
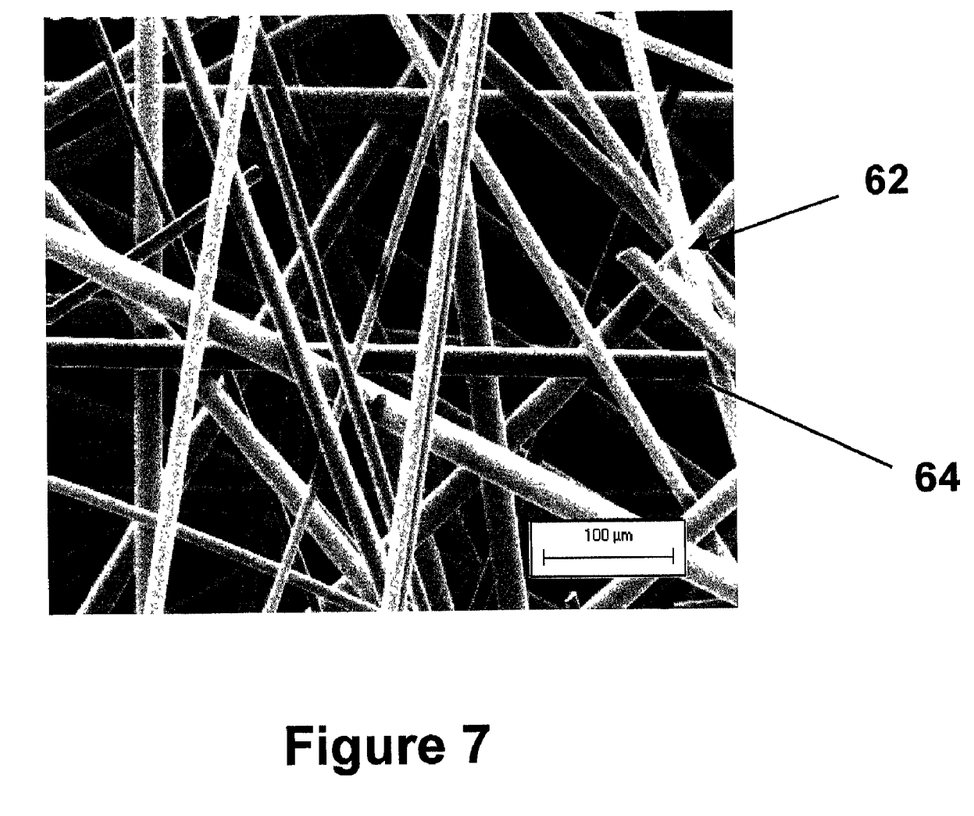
FIG. 7 is a micrograph of a nonwoven fiberous matrix comprising a first and a second absorbable glass fiber.

A scanning electron micrograph (SEM) of the nonwoven felt mat is showed in FIG. 7. Both first absorbable glass fiber 62 and second absorbable glass fiber 64 are seen in the SEM.

Three-dimensional nonwoven mats containing first and second absorbable glass fibers were also prepared in accordance with the procedure described in Example 1. However, as noted in Example 2, the structural integrity of the mat increased with the addition of PCL binder.

EXAMPLE 9

This example describes the preparation of pellets cut from an extruded cylinder of glass fiber nonwoven mats infiltrated with a polymer in order to make the nonwoven mats easier to handle.

A B-D 10 CC polypropylene syringe from Becton-Dickinson (Franklin Lakes, N.J.) was loaded with 0.33 grams of a nonwoven fiber mat composed of 50% first absorbable glass fibers and 50% second absorbable glass fibers as prepared in Example 8 without the addition of PCL binder. 5.65 grams of PCL polymer prepared with a monomer to initiator ratio of 16:1 was then loaded into the syringe in solid form. The syringe was heated to 60° C. to melt the polymer, and the melted polymer was forced to infiltrate the fiber bundle using the plunger of the syringe. The syringe was then cooled to room temperature. Once the polymer had solidified, the end of the syringe was cut off perpendicular to the direction of the syringe barrel using a razor blade, and the construct was extruded from the syringe using the plunger of the syringe. The cylindrical construct was then sliced into pellets using a razor blade. The actual amount of polymer used to infiltrate the fiber mat was less than 5.65 grams as there was excess resting above the construct after solidification.

Figure 8:
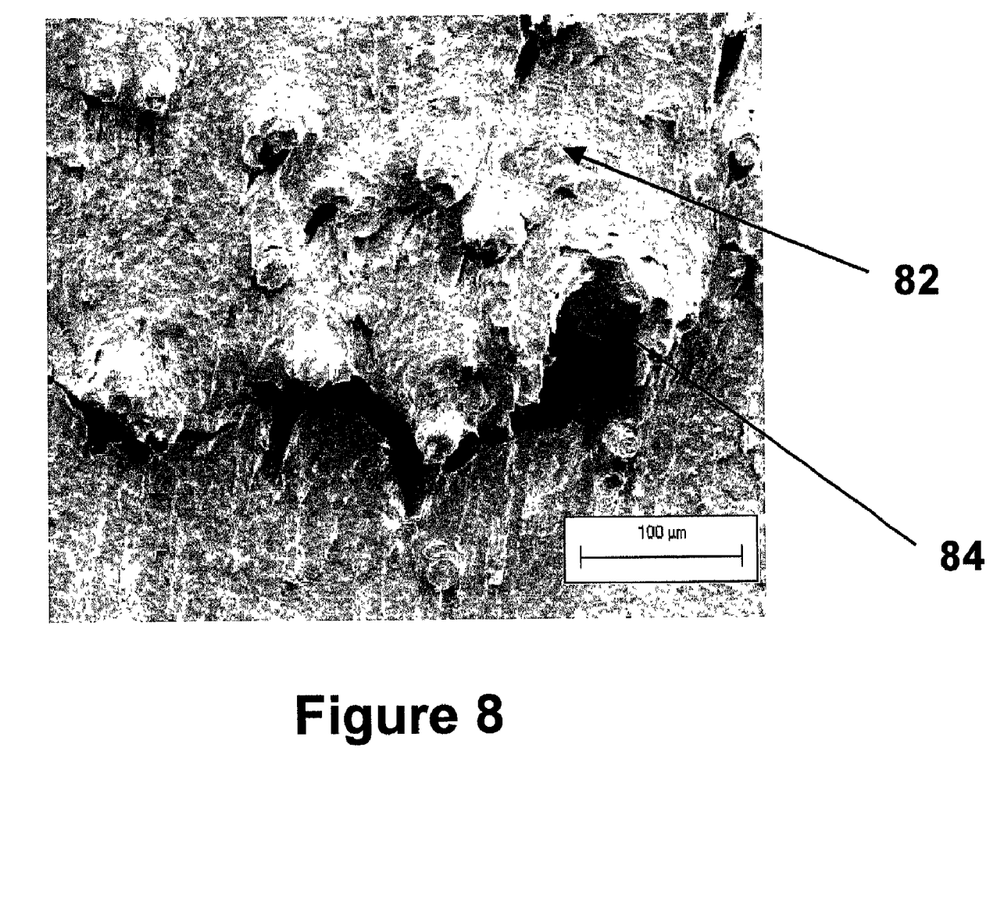
FIG. 8 is a micrograph of a nonwoven fiberous matrix comprising a first and a second absorbable glass fiber after infiltration with polycaprolactone (PCL).

A scanning electron micrograph (SEM) of a pellet is shown in FIG. 8. Polymer 82 infiltrated the nonwoven mat and coated the sharp glass fiber 84 ends. Such penetration provides the construct with the ability to maintain bundle coherence and retain potentially loose fibers, and the resulting discreet pellet morphology allows variable filling of a defect.

EXAMPLE 10

This example describes the preparation of glass/polymer fiber nonwoven mats infiltrated with polymer in order to impart handlability to the nonwoven mats.

0.22 grams of a glass/polymer fiber nonwoven mat composed of a mixture of 50 percent of the fiber by weight of the absorbable glass fiber, 25 percent by weight of the (95/5) PLA/PGA copolymer and 25 percent by weight of the (90/10) PGA/PLA copolymer, as prepared in Example 3, was placed in a 10-ml glass beaker. PCL polymer prepared with a monomer to initiator ratio of 16:1 was heated to 60° C. to melt the polymer. Five grams of melted polymer was poured onto nonwoven polymer/glass fiber mat in the glass beaker and allowed to cool until the polymer had solidified.

Figure 9:
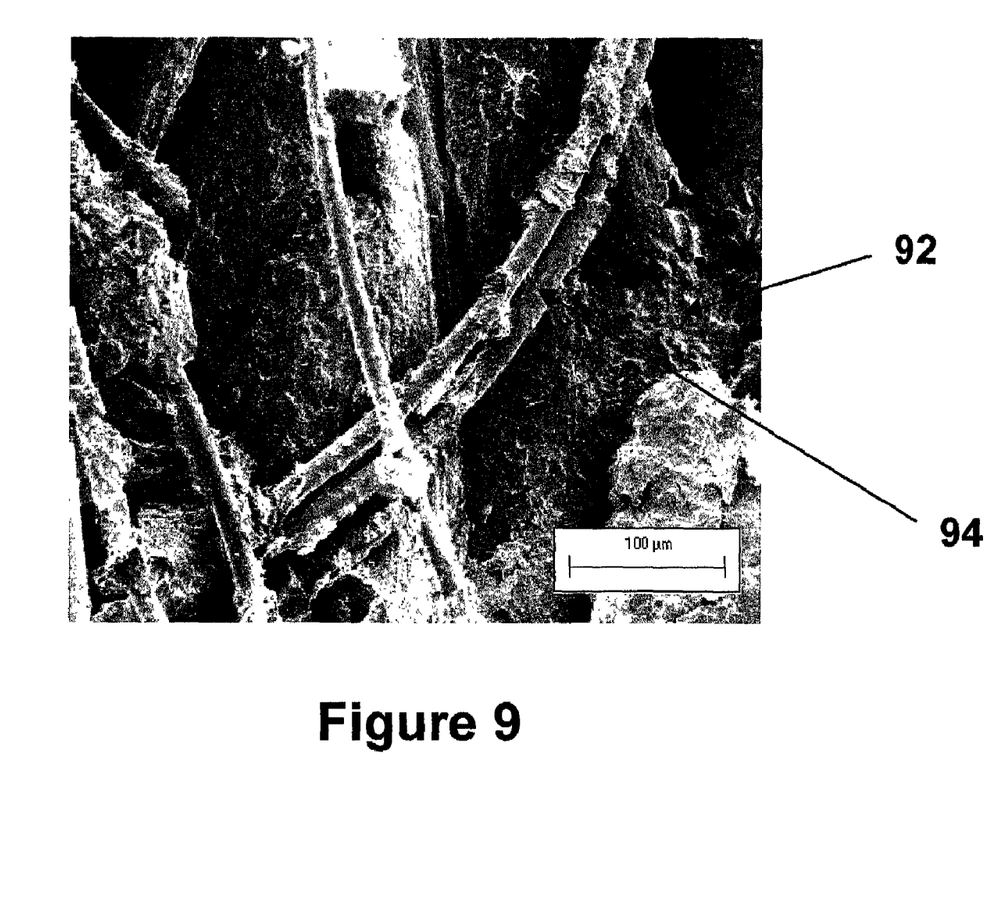
FIG. 9 is a micrograph of a nonwoven fiberous matrix comprising glass and polymer after infiltration with polycaprolactone (PCL).

In the resulting construct, the polymer infiltrated the nonwoven mat and coated the sharp fiber ends. The construct was sliced opened with a razor blade to determine polymer penetration into the nonwoven mat. A scanning electron micrograph (SEM) of sliced surface is shown in FIG. 9. The figure shows that polymer 92 fully penetrated the nonwoven mat of glass fibers 94. Such penetration provides the construct with the ability to maintain bundle coherence and retain potentially loose fibers.

EXAMPLE 11

This example describes the preparation of pellets cut from an extruded cylinder of glass/polymer fiber nonwoven mats infiltrated with a polymer in order to impart handlability to the nonwoven mats.

A B-D 10 OCC polypropylene syringe from Becton-Dickinson (Franklin Lakes, N.J.) was loaded with 0.15 grams of glass/polymer fiber nonwoven mat composed of a mixture of 50 percent by weight of the absorbable glass fiber, 25 percent by weight of the (95/5) PLA/PGA copolymer fiber, and 25 percent by weight of the (90/10) PGA/PLA copolymer fiber, as prepared in Example 3. 5.17 grams of PCL polymer prepared with a monomer to initiator ratio of 16:1 was heated to 60° C. to melt the polymer, then poured into the syringe. The melted polymer was forced to infiltrate the fiber mat using the plunger of the syringe. The syringe was then cooled to room temperature. Once the polymer had solidified, the end of the syringe was cut off perpendicular to the direction of the syringe barrel using a razor blade, and the construct was extruded from the syringe using the plunger of the syringe. The cylindrical construct was then sliced into pellets using a razor blade. The actual amount of polymer used to infiltrate the fiber mat was less than 5.17 grams as there was excess resting above the construct after solidification.

The polymer infiltrated the nonwoven mat and coated the sharp fiber ends. Such penetration provides the construct with the ability to maintain bundle coherence and retain potentially loose fibers, and the resulting discreet pellet morphology allows variable filling of a defect.

We claim:

1. An implantable, biodegradable device, comprising a fibrous matrix, said fibrous matrix comprising first fibers A and second fibers B, wherein fibers A biodegrade faster than fibers B, fibers A and B are present in relative amounts and are organized such that the fibrous matrix is provided with properties useful in repair and/or regeneration of mammalian tissue, wherein one of fibers A and B comprises a biodegradable polymer and one of fibers A and B comprises a biodegradable glass, and wherein the fibrous matrix comprises a gradient structure comprising a transition in the relative concentration of fibers A to fibers B.

2. The device of claim 1 wherein the rate of resorption of the fibrous matrix approximates the rate of replacement of the fibrous matrix by tissue.

3. The device of claim 1 wherein the weight ratio of fibers A to fibers B is from about 19:1 to about 1:19.

4. The device of claim 1 wherein the porosity of the fibrous matrix is effective to facilitate uniform tissue growth therein.

5. The device of claim 4 wherein pores ranging in size from about 20 microns to about 400 microns are interconnected and comprise from about 70 percent to about 95 percent of the fibrous matrix.

6. The device of claim 1 wherein the fibrous matrix comprises an organized network selected from the group consisting of threads, yarns, nets, laces, felts and nonwovens.

7. The device of claim 1 wherein the fibrous matrix comprises a configuration selected from the group consisting of a disk, a rectangle, a square, a tube and a star.

8. The device of claim 1 wherein the diameters of fibers A and fibers B range from about 5 microns to about 100 microns.

9. The device of claim 1 wherein fibers A and fibers B are bonded together by a biodegradable polymeric binder.

10. The device of claim 9 wherein the biodegradable polymeric binder is selected from the group consisting of polycaprolactone, polylactic acid, polydioxanone and polyglycolic acid.

11. The device of claim 1 wherein said fibrous matrix comprises a continuous transition from fibers A at the periphery of the device to fibers B at the center of the device.

12. The device of claim 1 wherein said fibrous matrix comprises a continuous transition from fibers A at the top of the device to fibers B at the bottom of the device.

13. The device of claim 1 wherein the fibrous matrix further comprises a biodegradable, fibrous polymeric coating.

14. The device of claim 13 wherein the biodegradable polymeric coating is selected from the group consisting of polylactic acid, polyglycolic acid, polycaprolactone and copolymers thereof.

15. The device of claim 1 wherein the fibrous matrix is chemically crosslinked or combined with hydrogels.

16. The device of claim 1 wherein the fibrous matrix is coated with an adhesive biological factor selected from the group consisting of fibronectin, vitronectin, V-CAM, I-CAM, N-CAM, elastin, fibrillin, laminin, actin, myosin, collagen, microfilaznent, intermediate filament, antibody, and fragments thereof; hyahironic acids, glycosaminoglycans, collagens, peptide fragments, pleiotrophin, endothelin and tenascin-C.

17. The device of claim 1 wherein the fibrous matrix is coated with a growth factor selected from the group consisting of members of TGF-β family, bone morphogenic proteins, fibroblast growth factors-1 and -2, platelet-derived growth factor-AA, and -BB, platelet rich plasma and vascular endothelial cell-derived growth factor.

18. The device of claim 1 wherein the fibrous matrix further comprises seeded or cultured therein cells selected from the group consisting of bone marrow cells, stromal cells, stem cells, embryonic stem cells, chondrocytes, osteoblasts, osteocytes, fibroblasts, pluxipotent cells, chondrocyte progenitors, osteoclasts, endothelial cells, macrophages, adipocytes, monocytes, plasma cells, mast cells, umbilical cord cells, leukocytes, epithelial cells, myoblasts, and precursor cells derived from adipose tissue.

19. The implant of claim 1, further comprising a fabric barrier layer formed on at least one surface of the implant.

20. The implant of claim 19, wherein the fabric barrier is formed on a top surface and a bottom surface of the implant.

21. The implant of claim 19, wherein the fabric barrier is a dense, fibrous fabric that is effective as a barrier to hyperplasia and tissue adhesion.

22. The implant of claim 21, wherein the fabric barrier is formed of an electrostatically spun aliphatic polyester.

23. The device of claim 1 wherein the biodegradable polymer is selected from the group consisting of aliphatic polyesters, poly(amino acids), copoly(ether-esters), polyalkylene oxalates, polyamides, poly(iminocarbonates), polyorthoesters, polyoxaesters, polyamidoesters, poly(anhydrides), polyphosphazenes and biopolymers.

24. The device of claim 1 wherein the biodegradable glass comprises a silicate-containing calcium phosphate glass.

25. The device of claim 1 wherein the biodegradable glass comprises a calcium phosphate glass wherein some of the calcium ions are replaced by ions selected from the group consisting of iron, sodium, magnesium, potassium, aluminum and zirconium.

26. The device of claim 1 wherein the biodegradable glass comprises from about 50 to about 70 weight percent phosphate, from about 0 to about 35 weight percent iron, with the remainder comprising calcium.

27. A device of claim 1 wherein the fiberous matrix is penetrated with a bioabsorbable polymer.

28. A device of claim 27 wherein bioabsorbable polymer used to the penetrate the fiberous matrix is selected from the group consisting of aliphatic polyesters, poly(amino acids), copoly(ether-esters), polyalkylene oxalates, polyamides, poly(iminocarbonates), polyorthoesters, polyoxaesters, polyamidoesters, poly(anhydrides), polyphosphazenes and biopolymers.

* * * * *